United States Patent [19]

Cabansag

[11] 3,933,154

[45] Jan. 20, 1976

[54] IMMOBILIZER DEVICE

[76] Inventor: Edwin M. Cabansag, 3937 Johnson St., Western Springs, Ill. 60558

[22] Filed: Jan. 15, 1974

[21] Appl. No.: 433,452

[52] U.S. Cl. ............................... 128/134; 269/328
[51] Int. Cl.² ........................................... A61F 5/37
[58] Field of Search ............ 128/134, 133, 75, 165; 269/328

[56] References Cited
UNITED STATES PATENTS

| | | | |
|---|---|---|---|
| 3,182,338 | 5/1965 | Shirrod | 128/134 |
| 3,315,671 | 4/1967 | Creelman | 128/134 |
| 3,358,141 | 12/1967 | Hoffman | 128/134 |
| 3,526,222 | 9/1970 | Dreibelbis | 128/134 |
| 3,606,885 | 9/1971 | Lund | 128/134 |
| 3,650,523 | 3/1972 | Darby | 128/134 |
| 3,724,453 | 4/1973 | Dixon | 128/134 |
| 3,729,752 | 5/1973 | Huggins | 128/134 |

Primary Examiner—Robert W. Michell
Assistant Examiner—Lee S. Cohen
Attorney, Agent, or Firm—Laff, Whitesel & Rockman

[57] ABSTRACT

The invention provides an immobilizer for use in X-ray, and surgical procedures. The immobilizer has a back which is adapted to be rigid or bent at various positions. It also has flexible straps for securing different sections of a patient's body against movement in the immobilizer. The immobilizer comprises two parts, a radiotransparent backing member and a radiotransparent flexible part. The backing member is removably inserted under the flexible member with the backing member held firmly by loops and slots on the back of the flexible member. The knee and elbow sections can be produced so as to be used individually and have a unique method of restraining these appendages. The elbow and head restraints are adjustable for patients of different heights.

22 Claims, 16 Drawing Figures

IMMOBILIZER DEVICE

This invention relates to immobilizers, and in particular to immobilizers for use in X-ray and surgical procedures.

The uncooperative patient is a problem in many hospitals today. This is especially so when attempting to obtain an X-ray of an infant or small child. If the infant or child is not maintained in an immobile posture during exposure, the X-ray must be re-taken, thus exposing the patient to additional harmful radiation, besides wasting the cost of film and the time of the X-ray technician. It is also difficult to restrain a subject during surgical procedure.

To alleviate this problem, various methods and apparatus have been devised to restrain the patient. Once restrained, movement of a portion or all of the patient's body is prevented and the necessary procedure can be undertaken. Present restraints used by hospitals have several disadvantages. An important disadvantage is that the restraining device could interfere with the necessary procedure. A further disadvantage is that once restrained, it is generally extremely difficult to change the position of the patient as may be required during the procedure. A further disadvantage is that most restraining means only restrain a portion of the body. To restrain additional parts of the body, a second or even a third method must be employed. Another disadvantage is that the restraining methods presently used are generally quite clumsy and may require several people to apply the restrainer to the patient. Yet another disadvantage is that most immobilizers require a considerable amount of storage space, which hospitals can ill afford. A further disadvantage is the high cost of maintaining a stock of different length restrainers, for subjects of different lengths.

Beyond these disadvantages, important problems are posed by the unique requirements of special situations. For example, during special X-ray or surgical procedures, it is often necessary to insert fluids and tubes into various parts of the body. As another example it is often necessary to bend the patient to different angles and degrees at different parts of the body. Either way, there is a problem because most restrainers cannot restrain the whole body and yet be contoured for various functions. It is not practical to use several restraining methods and devices to attain this end.

Hence, there is a need for an improved restrainer-immobilizer, most particularly one which can be contoured and used for most X-ray and surgical procedures.

Accordingly an object of this invention is to provide a new and improved restrainer for immobilizing patients during various procedures. A more particular object is to provide an immobilizer which can be used during X-ray and surgery and will not interfere with the procedure.

Still another object is to provide a restrainer which can immobilize the whole body of a patient or any part thereof.

Yet another object is to provide an immobilizer which is flexible enough to be used in almost all procedures.

A further object is to provide a restrainer which is inexpensive and can be used for all patients in almost any position.

Still another object is to provide an economical and efficient means of restraining a patient during medical procedures.

In keeping with an aspect of this invention, these and other objects are accomplished by providing a flexible restrainer having a removable radiotransparent backing member. The backing member is adjustable to be either rigid or partially flexible. For rigidity, radiotransparent connecting means are held within channel means on the back portion of the restrainer backing member and for flexibility all or anyone of the connecting means may be removed. Covering the radiotransparent backing and connecting means when they are in place is a one piece radiotransparent member having a plurality of flexible straps attached. The one piece flexible member has an aperture disposed in the anal region for insertion of tubes for various procedures. The flexible straps are adapted to be attached over different parts of the patient's body to assure complete restraint of the bodily parts. The elbow and knee restraints are provided with means for drawing the straps tight around each limb to secure such limb against movement. The elbow restraint position can be changed to accomodate different procedure. People of different heights are accomodated by a head restraint and an arm restraint which can be adjusted to different positions.

The nature of the preferred embodiment will be understood best from a study of the attached drawings, in which.

Figure 2:
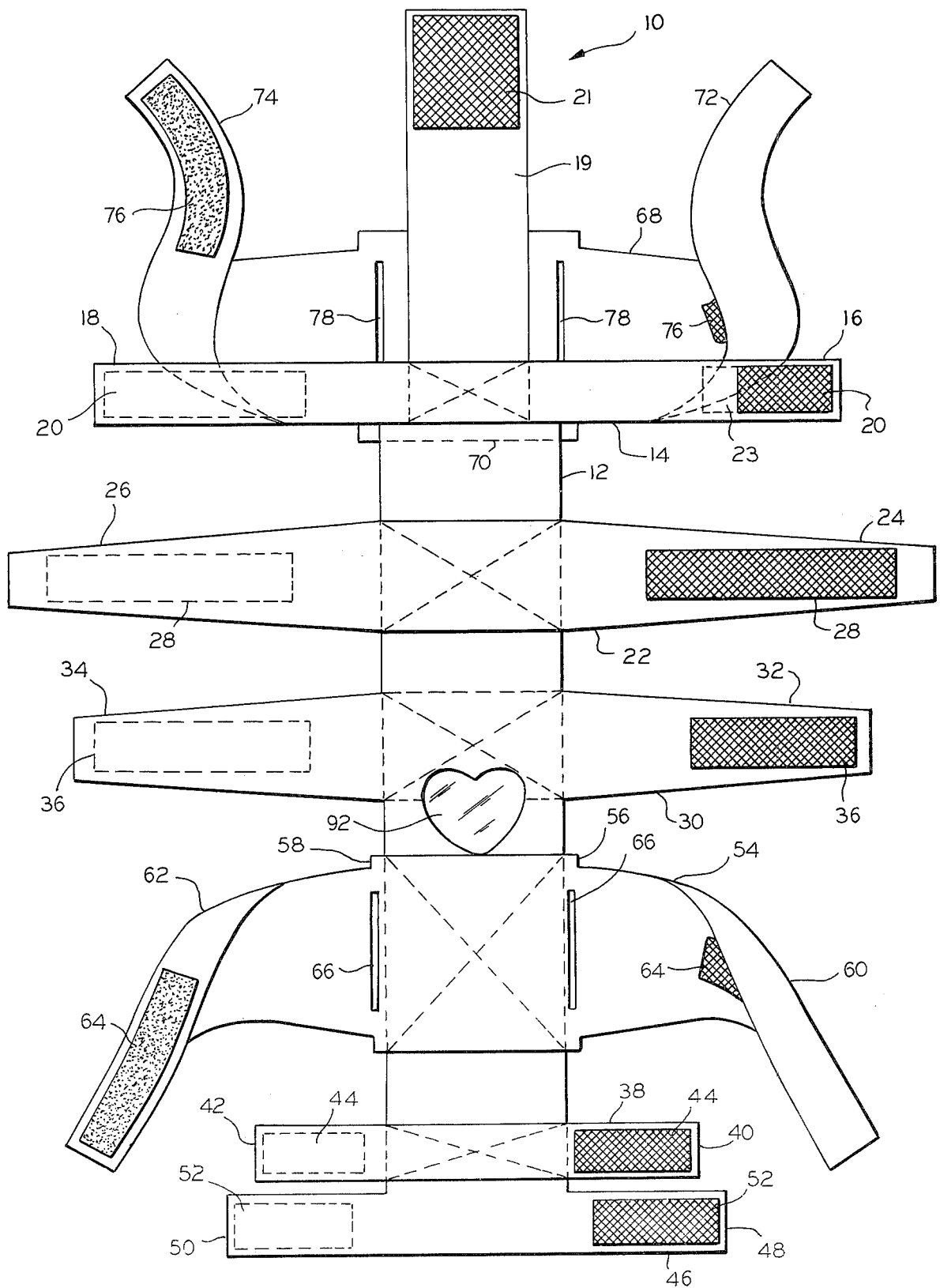
FIG. 2 is an overview of the complete immobilizer device, having the restraining straps open without a child, and the elbow restraints being pivoted in the head position.
Figure 8:
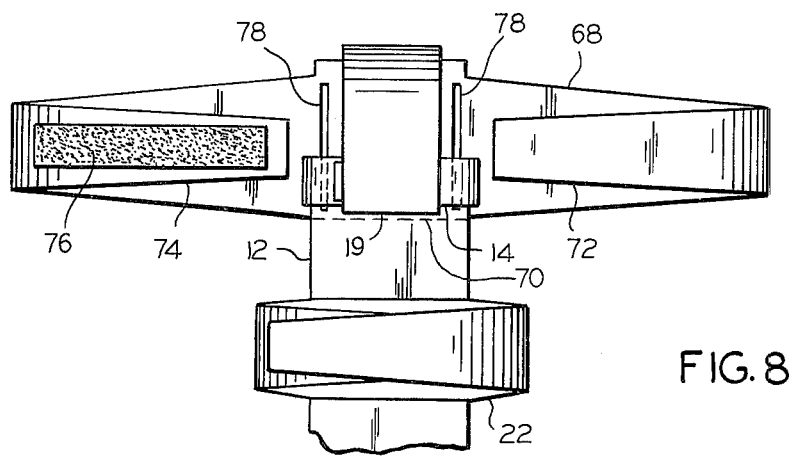
FIG. 8 is a detail of the elbow restraint pivoted to a position whereby the child's arms are held above its head.
Figure 8A:
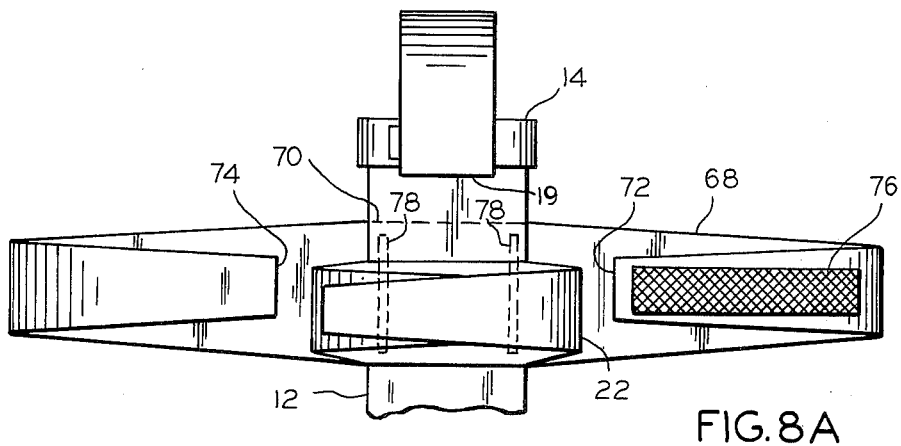
FIG. 8A is a detail of the elbow restraint of FIG. 8 pivoted to hold the child's arms at the side of its body.

Referring to the drawings, and particularly to FIG. 2, the immobilizer of an embodiment of my present invention is designated by the numeral 10, and comprises a generally longitudinal flexible radiotransparent member 12 which is of a size to generally extend along the length of a youthful patient to be X-rayed or subjected to surgical procedures. Flexible member 12 may be made of any pliable material such as canvas, cloth or the like, or any disposable material which provides the necessary strength to restrain a subject placed therein.

Extending at approximately right angles from the axial length of flexible member 12 are a plurality of restraining means comprising, in the preferred embodiment, a plurality of straps. These straps may form part of flexible member 12, or may be sewn or otherwise attached to the flexible member 12 at their midsection. The latter construction is illustrated in FIG. 2, whereby the straps are shown as being sewn to flexible member 12 at their approximate midpoint.

Strap 14 is attached to the approximate upper end of flexible member 12 and has a pair of ends 16, 18 extending laterally outwardly. Each end 16, 18 has self attachment means 20 on correspondingly mating sides thereof, such that when the ends 16, 18 are brought into overlapping contact with one another, they will adhere one to the other. For example, self attachment means can comprise Velcro fasteners. Extending vertically from the point of attachment of strap 14 to flexible member 12 is a head restraining strap 19 having self-attachment means 21 attached thereto. Self attachment means 21 is adapted to mate with and adhere to a self-attachment means 23 applied to the underside of end 16 of strap 14, as seen in FIG. 2, when strap 14 is extended over the forehead of a patient, as will be explained.

Located at a distance below strap 14 is a similarly constructed strap 22 having a pair of ends 24, 26 and self attachment means 28 affixed thereto on correspondingly mating surfaces. Strap 30, similarly constructed with a pair of ends 34, 34 and self attachment means 36, is affixed to flexible member 12 at a distance below strap 22. Similarly, strap 38, having ends 40, 42, and self attachment means 44, and strap 46 having ends 48, 50 and self attachment means 52 are attached to flexible member 12 adjacent, and at, the lower end of the flexible member, respectively.

Figure 9:
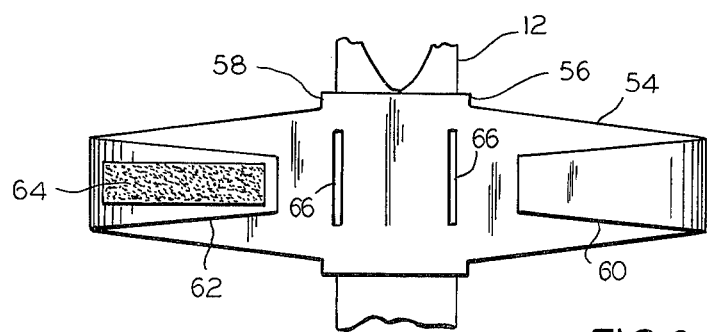
FIG. 9 is a detail view of the inventive knee restraint forming part of the present invention.

Located between straps 30 and 38 is strap 54 which is somewhat wider than the previously described straps at its points of attachment at bases 56, 58 to flexible member 12. As seen in FIGS. 2 and 9, strap 54 has two tapered ends 60, 62, and self attachment means 64 affixed thereto as described in conjunction with the other straps of my invention. Slots 66 are disposed adjacent bases 56 and 58 of strap 54, and are adapted to receive the ends 60, 62 respectively, which ends may be pulled through the slots to form loops through which a child's knees may pass. By pulling the ends 60, 62 through the slots 66, the loops may be adjusted to secure the knees of any size child, as will be explained.

Referring to FIGS. 2, 5, 8, and 8A, there is shown an elbow restraining strap 68 adapted to be disposed in two alternate positions. The strap 68 is attached along its edge 70 (FIG. 5) to the back of flexible member 12. Since the straps and body of my immobilizer are made of a flexible material, strap 68 is adapted to pivot about edge 70, as will be further explained.

Figure 5:
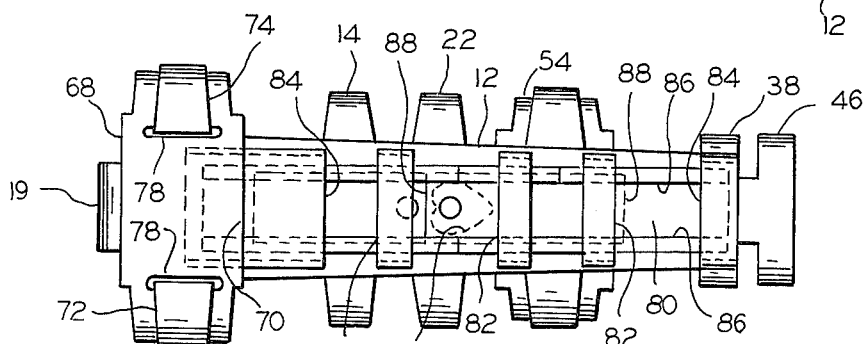
FIG. 5 is a rear view of the inventive immobilizer device showing the radiotransparent backing member and the connecting means within the channels.

Referring to FIG. 2, strap 68 comprises two tapered ends 72, 74 having self attachment means 76 affixed to correspondingly mating surfaces thereof. At the bases of ends 72, 74 are a pair of slots 78 adapted to receive the ends 72, 74 when passed therethrough (FIG. 5). Ends 72, 74 may pass through slots 78 in either direction, depending upon whether the child's arms are to be restrained at its side, or over its head, as will be explained.

Referring to FIG. 5, the adjustable rigid backing member 80 of my immobilizer and its relation to flexible member 12 will be described. The rear of flexible member 12 includes a plurality of loop members 82 forming a passage thereunder. Toward either end of the rear of flexible member 12 are a pair of pockets 84. A rigid backing member 80 is held in place adjacent flexible member 12 by being inserted beneath loops 82. The ends of backing member 8 are inserted in pockets 84 to restrain the backing member against longitudinal movement.

Backing member 80 may be a single rigid radiotransparent element, such as a single piece of wood, plastic, or the like. However, in the preferred embodiment, rigid backing member 80 is formed in three sections to permit the patient to bend at the pelvic region and/or knees if desired. To this end, referring to FIG. 5, the backing member 80 includes channel means 86 extending along the length thereof. Connecting means 88 are adapted to fit into the channel means of two adjacent sections of rigid backing member 80, and function to hold the sections together. Holes 90 are disposed in each of connecting means 88 to permit the connecting means to be slidably removed by hand by sliding same in channels 86, whereby one section of the rigid backing member is free to move relative to its adjacent section.

As seen in FIGS. 2 and 5, an aperture 92 is centrally located at the approximate longitudinal midpoint of immobilizer 10. Aperture 92 extends through rigid backing member 80 and flexible member 12 to permit medicinal materials to be inserted in the anal area of the patient while the patient remains restrained. In addition, tubes or other apparatus could be inserted in the patient through aperture 92 as required in special X-ray or surgical procedures.

Figure 1:
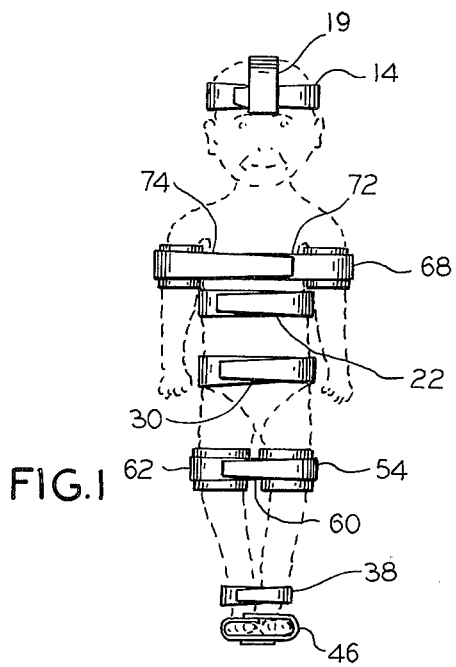
FIG. 1 is an overview of a child in the inventive immobilizer device with the straps closed and the child's arms at its side.

The operation of the embodiment of my invention disclosed in FIGS. 1–5, 8, 8A, and 9–12 is as follows: The immobilizer 10 is prepared for use in securing a child against movement for an X-ray or surgical procedure by first opening or disengaging all of the straps and laying the immobilizer flat on a horizontal surface, similar to the position shown in FIG. 2. If the child is to be restrained with its arms at its side, as illustrated in FIG. 1, elbow restraining strap 68 is pivoted about edge 70 (FIG. 5) such that it is in the position shown in FIG. 8A. The subject to be restrained is positioned atop the immobilizer such that the axis of flexible member 12 extends along the length of the subject.

With the child in position on immobilizer 10, ends 16, 18 of strap 14 are extended forward across the subject's forehead and are held together by self attachment means 20. End 16 is placed atop end 18 so that self attachment means 23 faces upward. It is apparent that self attachment means 20 can secure ends 16, 18 together at any longitudinal position of the strap ends, thereby allowing strap 14 to accomodate children of any size. The same is true for the other restraining straps forming part of my invention.

With the forehead of the subject so restrained, strap 19 is extended forward across the head from the back and self attachment means 21 is fastened to self attachment means 23. In this manner, the subject is restrained from axial movement relative to immobilizer 10, and the head is restrained against movement.

Figure 4:
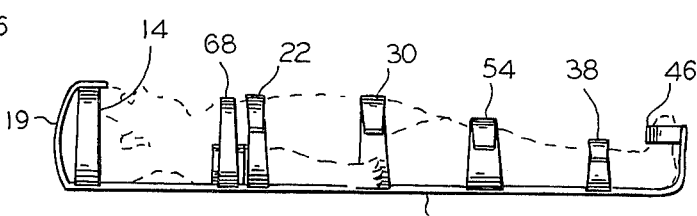
FIG. 4 is a side view of a child in the inventive immobilizer in a horizontal position with the straps closed and the child's arms at its side.

Next, strap 22 is extended across the chest of the subject, and the ends thereof are held together by self attachment means 28. In similar fashion, strap 30 is extended forward and fastened across the subject's torso, and strap 38 is extended forward and fastened across both ankles of the infant or child. Strap 46 passes under the bottoms of the feet of the child and is extended forward and fastened across the feet (FIGS. 1, 4).

My invention also provides a unique and efficient means for restraining the elbows and knees of the subject such that each limb is individually restrained, and simultaneously both limbs, either elbows or knees, are held jointly against movement. To restrain the subject's elbows in the position shown in FIG. 1, ends 72 and 74 of strap 68 are extended over each elbow of the subject, and the ends are then passed through each respective slot 78. The ends 72, 74 are then drawn through slot 78 so as to tightly engage the elbow in the loop thus formed. It is apparent that in this manner, the loops formed by strap 68 can be adjusted to accomodate subjects of varying sizes.

Figure 10:
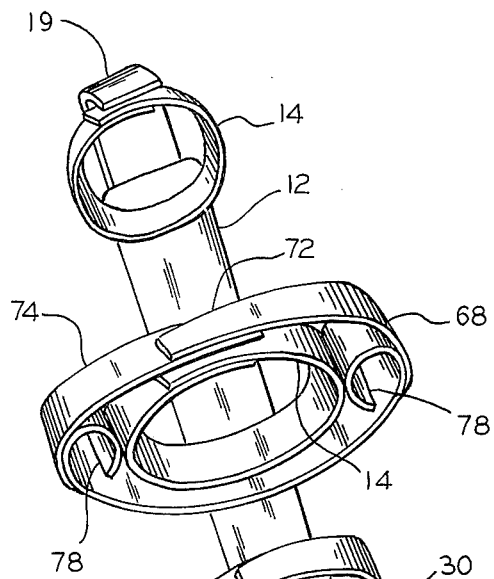
FIG. 10 is a perspective view of the inventive immobilizer device of FIG. 2 with all straps closed.
Figure 12:
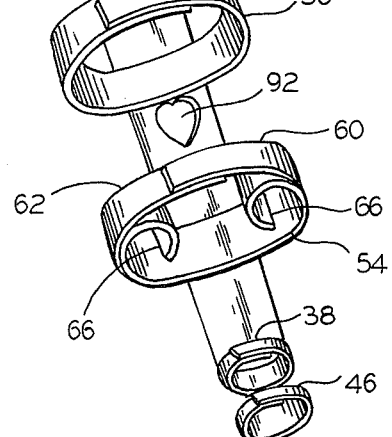
FIG. 12 is a side view of the immobilizer device showing a child seated and secured against movement in the device.

Next, the ends 72, 74 of strap 68 are passed outward relative to flexible member 12, and extended over and around the elbows until the self attachment means 76 on each of the ends adhere to each other across the chest of the subject. FIG. 1 illustrates how the elbow restraint means looks with the subject in the immobilizer, while FIG. 10 illustrates how the straps of the immobilizer look when engaged, but with the subject removed for descriptive purposes. In this manner, each individual elbow is restrained against movement, and both elbows are secured against the side of the subject. With the elbow held against movement, the entire arm is restrained, since it is extremely difficult, if not impossible for a child to move any part of its arms while the elbows are so restrained.

Figure 3:
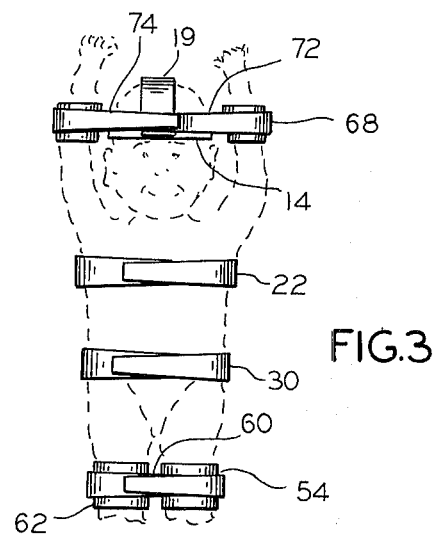
FIG. 3 is an overview of a child in the inventive immobilizer device with the straps closed and the child's arms held above its head.

For purposes of certain X-ray or surgical procedures, it may be desirable to restrain the subject's arms in position over its head. For example, in taking a lateral X-ray exposure of the chest or abdominal region, it is necessary that the bones of the arms do not appear in the negative. As illustrated in FIG. 3, my invention is readily adaptable to hold the subject's arms above its head and against movement. Prior to laying the subject on immobilizer 10 as previously described, strap 68 is pivoted upward about edge 70 such that it is in the positon shown in FIG. 8. The subject's arms are located over its head, and the ends 72, 74 of strap 68 are extended over and around the elbows and passed through slots 78 as previously described. Ends 72, 74 are next extended outward, over the elbows, across the forehead of the subject, and brought into contact such that self attachment means 76 cause the ends to be fastened together. In this manner, both elbows are individually restrained against movement, and at the same time, are held together against the child's head.

Knee restrainer strap 54 is similar to elbow strap 68 in configuration and operation. Referring to FIGS. 1, 9, and 10, with the subject laying in immobilizer 10, ends 60 and 62 of strap 54 are extended over and around the subject's knees, and passed through the respective slots 66. Next, the ends are extended outward, over, and around each knee and joined together by means of self attaching means 64. In this manner, each knee is held against movement and both knees are restrained relative to flexible member 12 and rigid backing member 80.

It is to be understood that immobilizer 10 is designed such that aperture 92 is located adjacent the anal opening of the subject, such that medicine or surgical instruments may be applied to the subject while restrained.

Figure 6:
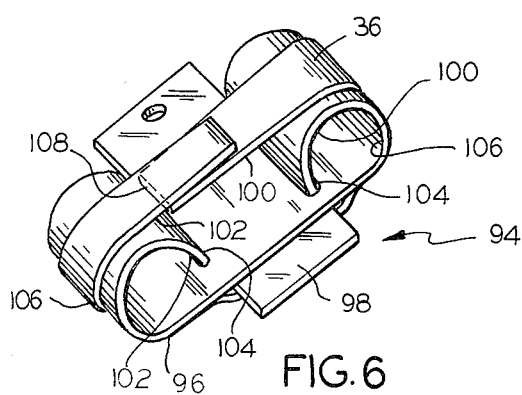
FIG. 6 is a general view of the elbow restraining device forming part of the present inventive concept.

Various additional embodiments of my inventive concept are disclosed in FIGS. 6, 7, 13, and 14. FIG. 6 discloses an individual immobilizer apparatus 94 for restraining the elbows and chest of a patient to be X-rayed comprising a strap member 96 attached to a relatively short rigid backing member 98. Strap 96 includes two tapered ends 100, 102, and slots 104 adjacent the base of tapered ends 100, 102. The ends of strap 96 are adapted to extend through their respective slots 104 to form loops 106 through which the elbows of the patient extend. The ends 100, 102 are drawn tightly through the slots 104 until the loops 106 are drawn small enough to tightly engage the patient's elbows. Ends 100, 102 after passing through slots 104 are then extended forward across the chest of the patient and joined together by self attaching means 108 applied to corresponding mating surfaces of the strap ends. In this manner, immobilizer apparatus 94 tightly secures the patient's elbows against its sides, preventing movement of the elbows and arms.

Figure 7:
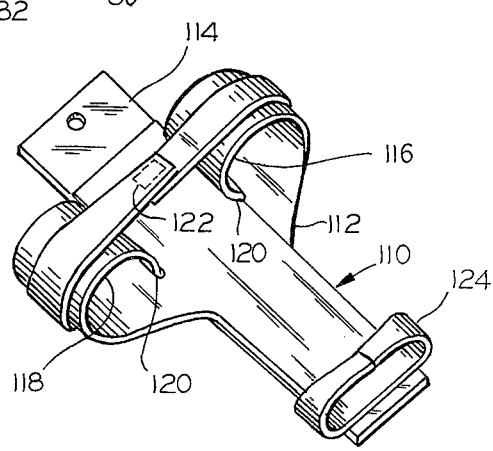
FIG. 7 is a general view of the knee-ankle restraining device forming part of the present inventive concept.

The immobilizer apparatus 110 of FIG. 7 is similarly constructed, and is modified to restrain the knees and ankles of the patient against movement. Immobilizer 110 comprises a strap element 112 fixed to a rigid backing member 114. Tapered ends 116, 118 pass through slots 120 and extend forward across the knees of the patient after being drawn tightly around the knees of the patient. Self attachment means 122 on correspondingly mating surfaces of ends 116, 118 hold the strap ends firmly together. At one end of backing member 114 is an additional strap member 124 with self attaching ends adapted to extend around and secure the patient's ankles against movement. By means of immobilizer apparatus 110, the knees and ankles, and therefore the legs and hips of the patient are held rigid for X-ray or surgical procedures.

Figure 11:
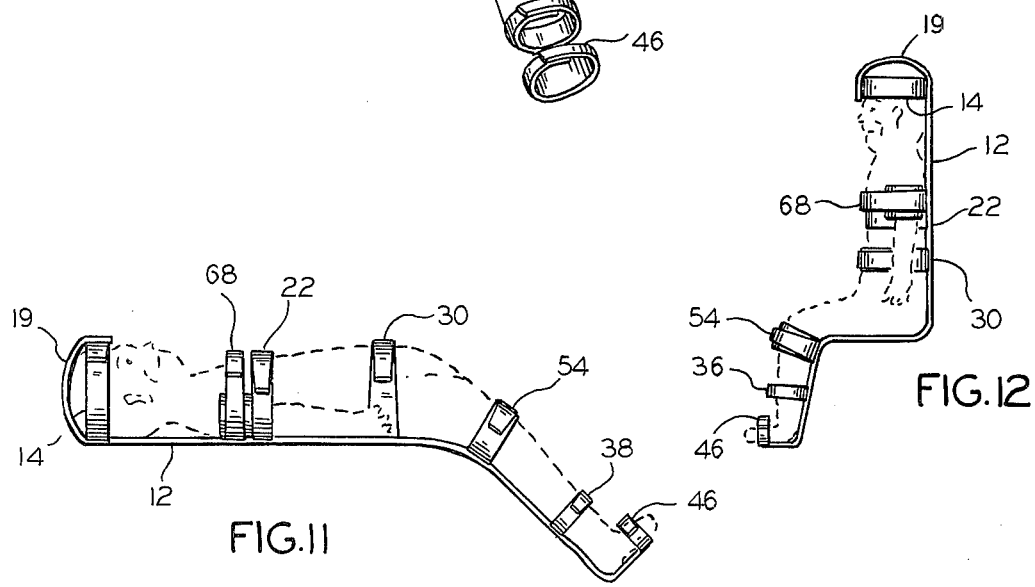
FIG. 11 is a side view of the inventive immobilizer device with a child restrained therein and bent at the knees and pelvic region.

In the present invention, means are provided to position the subject in various positions other than rigidly straight. By removing one of the connecting means 88 of backing member 80, the subject is allowed to bend backward at the knees (FIG. 11). Likewise, by removing the other connecting means 88, the subject is permitted to bend forward at the hips. In this manner, the subject may be restrained while in a seated position (FIG. 12), or may be placed on its side with the bent portions of the body providing support for retaining the subject in the lateral position.

Figure 15:
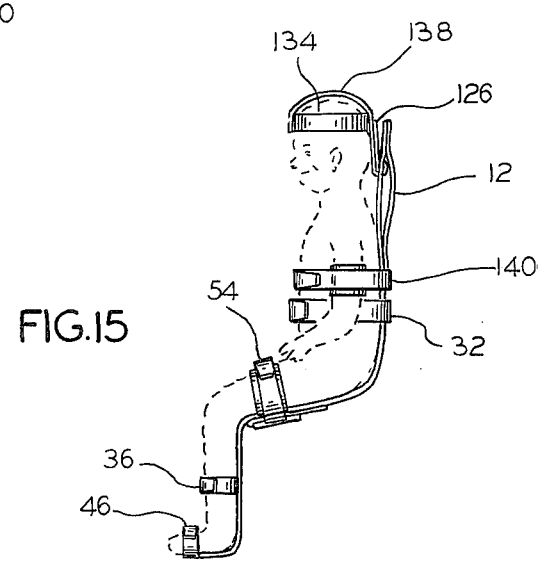
FIG. 15 is a top view of a horizontally disposed child using the adjustable head restraint and the sliding elbow restraint of FIGS. 13 and 14, with the rigid backing member removed from the flexible restraining means.

In addition, it has been discovered that my immobilizer will restrain a subject against movement in some positions with backing member 80 removed from flexible member 12. In FIG. 15, the subject is illustrated lying on its side, completely strapped in immobilizer 10, with rigid backing member 80 removed. The subject is bent at the hips and knees to form a position which supports the subject in the lateral position. Because the elbows and knees of the subject are held against individual and joint movement, it is very difficult for the subject to move, even through the rigid backing member is not used.

Figure 13:
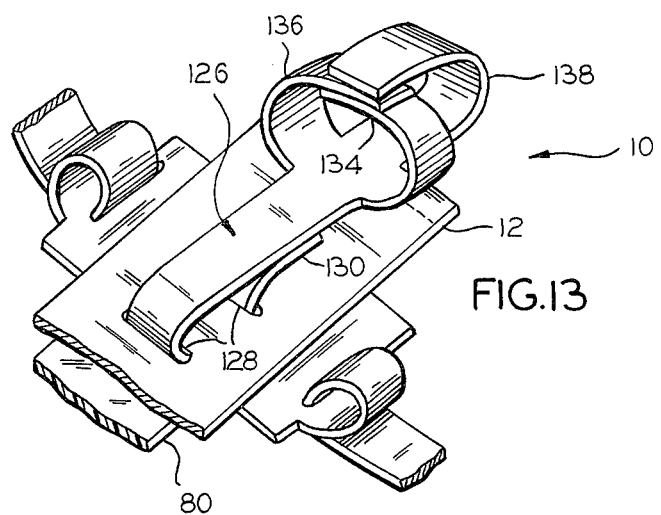
FIG. 13 is a perspective view of an alternative embodiment of my invention including an adjustable head restrainer.
Figure 14:
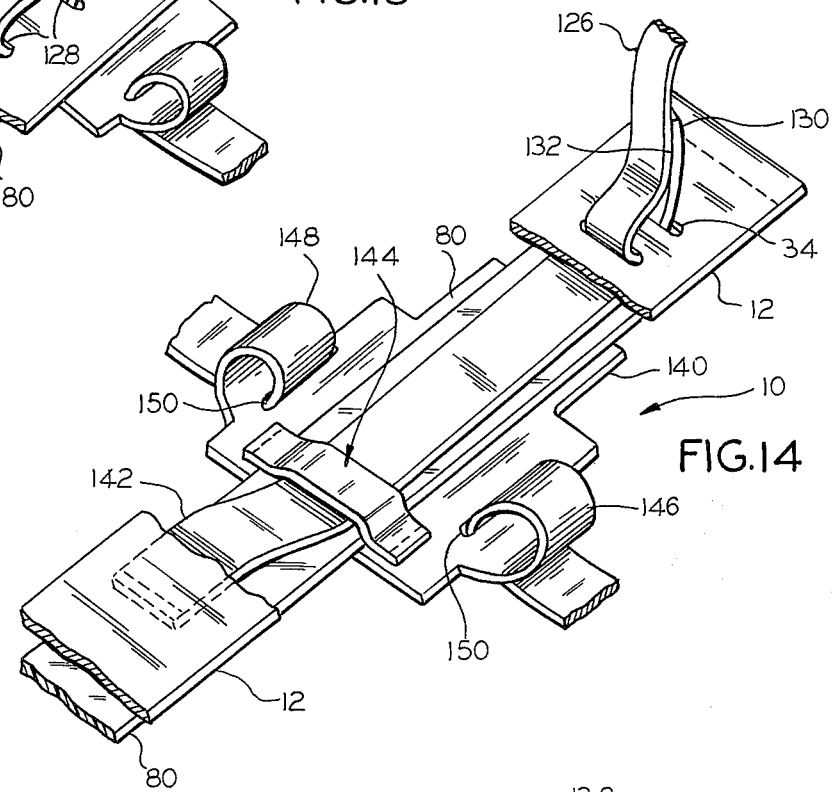
FIG. 14 is a perspective view of still another alternate embodiment of my invention including a sliding elbow restraint.

An alternative embodiment of the immobilizer of FIG. 2 is illustrated in FIGS. 13 and 14 wherein the head restraining strap is adapted for longitudinal displacement to accomodate subjects of varying heights. Referring to FIG. 13, there is shown a strap 126 looped through a pair of slots 128 disposed towards the head end of flexible member 12. The end of strap 126, designated by the numeral 130, doubles back adjacent strap 126 and is removably adhered thereto by self attaching means 132 (FIG. 14). The upper portion of strap 126 includes lateral strap means 134, 136 which are adapted to extend around and fasten across (by self attaching means, not shown) the subject's forehead similar to ends 16, 18 of strap 14 of FIG. 2. Also, head strap 138 extends from the top of strap 126 and is adapted to extend over the head of the subject and be fastened to strap 136 in the same manner that strap 19 of FIG. 2 adheres to end 16 of strap 14.

Referring to FIG. 13, the longitudinal position of strap 126 is adjusted by disengaging end 130 from its mating surface of strap 126, and positioning strap 126 in slots 128 such that straps 134, 136 and head strap 138 firmly engage the subject's head and forehead. When the proper position has been attached, end 130 is again pressed against strap 126 and self attaching means 132 causes strap 126 to be maintained in place.

An additional embodiment of my invention is disclosed in FIG. 14 wherein the elbow restraining means of immobilizer 10 are adapted for longitudinal movement to accomodate subjects of varying sizes. To this end, strap 68 of FIG. 2 is replaced with strap 140, except that strap 140 is not directly affixed to flexible member 12 as is strap 68. A lengthwise strap element 142 is attached at either end to the side of flexible member 12 adjacent rigid backing member 80. An additional lateral strap element 144 extends across strap 140 and extends over both strap element 142 and rigid backing member 80. It is apparent from viewing FIG. 14 that strap 140 is free to move along strap element 142 and backing member 80 to adjust to various longitudinal positions. Since strap 14 is made of a flexible material such as canvas or the like, it is able to pivot just above strap 144 into the positions shown in FIGS. 8 and 8A. Strap 140 also includes ends 146, 148 which extend through slots 150 in the same manner, and for the same purpose as described previously in conjunction with the elbow restraining means 68 of FIG. 2.

While it is not illustrated, it is understood that knee restrainer 54 of FIG. 2 can be adapted for variable longitudinal movement by using the same construction as described in conjunction with the embodiment of FIG. 14. In this manner, the knee restraining means of my invention may be positioned to fit subjects of varying sizes.

When all straps of the restraints have been mated, the patient is totally immobilized. Movement by the patient of his body is substantially completely restricted, thereby allowing the X-ray technician or physician to turn the patient in any direction; to bend the patient as is necessary, or manipulate the patient in the necessary manner.

From the foregoing detailed description, it will be evident that there are a number of changes, adaptations and modifications of the present invention which come within the province of those skilled in the art. However, it is intended that all such variations not departing from the spirit of the invention, be considered as within the scope thereof as limited solely by the appended claims.

I claim:

1. An immobilizer for use in X-ray or surgical procedures on a patient comprising:
    a completely flexible radiotransparent member including flexible restraining means,
    said flexible member having a front surface adapted to extend longitudinally adjacent the posterior of said patient and a posterior surface;
    said restraining means adapted to extend around portions of said patient and secure said patient to said flexible member and against mvoement; and
    a rigid radiotransparent backing member removably attached to one of said surfaces of said flexible radiotransparent member to alternatively provide a rigid support for said member when desired.

2. The immobilizer of claim 1 wherein said rigid radio-transparent backing member comprises a plurality of inflexible support elements removably joined by radiotransparent connecting means to form, alternately, a rigid unitary support element for said flexible member when connected, and individual support elements for predetermined sections of said flexible member when disconnected, whereby said immobilizer is capable of flexibly bending between said sections when said backing member is in said latter configuration.

3. The immobilizer of claim 2 wherein said inflexible support elements each include channel means,
    said radiotransparent connecting means being slidably disposed in said channels for movement therein, whereby said connecting means are inserted in said channels to form said rigid unitary support element, or removed to permit said flexible radiotransparent member to bend.

4. The immobilizer of claim 2 wherein said restraining means is adapted to restrain a patient by engaging and securing various portions of said patient's body against movement;
    said connecting means including at least one slidable member which when removed permits said patient to bend at the pelvic region.

5. The immobilizer of claim 4 wherein said connecting means includes an additional slidable member which, when removed, permits said patient to bend at the knees.

6. The immobilizer of claim 1 wherein said restraining means includes:
    a plurality of pairs of straps;
    each strap of each said pair adapted to overlap the other strap of said pair in a mating relationship when said straps are extended over said patient; and
    fastening means provided along the surfaces of said straps to secure said straps in said mating relationship for securing said patient in said immobilizer.

7. The immobilizer of claim 1 wherein said flexible radiotransparent member includes:
    loop means extending posterior of said flexible radiotransparent member and extending around and attaching said rigid backing member to said flexible member; and pocket means fixed adjacent either end of the posterior of said flexible member, said pocket means receiving the uppermost and lowermost ends of said rigid backing member to prevent lengthwise movement of said rigid backing member.

8. The immobilizer of claim 1 wherein said flexible member and said backing member comprise mating apertures located adjacent one another to provide access for injecting medicinal or other materials into the anal portion of said patient.

9. The immobilizer of claim 1 wherein said flexible restraining means includes a plurality of flexible strap means disposed lengthwise of said flexible member in spaced relation adjacent portions of said flexible member disposed to correspond to the head region, chest region, abdomen region, knees, ankles, and elbows of said patient;

said chest, abdomen, knee, elbow and ankle corresponding portions of said restraining means each comprising a pair of strap members with mating means on at least one surface of said strap members to secure the ends of said strap members together when disposed around a portion of said patient;

said head region restraining means comprising an additional pair of strap members with mating means on at least one surface of one strap member adapted to extend over the forehead of said patient and fasten to the other head strap member.

10. The immobilizer of claim 1 wherein said restraining means comprises pairs of straps attached to said flexible member with mating means on at least one surface of each strap to secure the ends of said straps together when disposed around a portion of said patient;

said straps disposed to correspond to the knee and elbow locations of said patient, said straps having slots spaced from the point of attachment to said flexible member;

said ends of said straps adapted to be looped through said slots to provide adjustable restraining means for the limbs of said patient;

said ends of each said strap extending around the region of a portion of the limb to be immobilized, passing through its respective slot, drawn tightly around said region of said limb portion, and passing again around and over said limb region to attach to said other of said pair of straps;

said elbow restraining means including a loop on the posterior surface of said flexible member and extending across said flexible member;

said loop providing slidable movement of said elbow restraining means relative to said flexible member.

11. The immobilizer of claim 1 wherein said restraining means includes elbow restraining means pivotally attached to said flexible member whereby said elbow restraining means is alternatively disposed in a first position whereby the elbows of the patient are secured against movement adjacent and alongside the torso of said patient, and pivotally movable to a second position whereby the elbows of the patient are secured against movement alongside the head of said patient.

12. The immobilizer of claim 11 wherein said elbow restraining means is pivotally attached along a transverse axis to the posterior of said flexible member and is adapted to pivot about said axis to move between said first position and said second position, said elbow restraining means including:

pairs of straps attached to said flexible member with mating means on at least one surface of each strap to secure the ends of said straps together when disposed around the elbow of said patient;

said straps having slots spaced from the point of attachment to said flexible member;

said ends of said straps adapted to be looped through said slots to provide an adjustable restraining means for the elbows of said patient.

13. The immobilizer of claim 12 wherein said straps extend across a region of said flexible member corresponding to the chest of said patient and attach to each other when said elbow restraining means is in said first position, whereby said elbow restraining means simultaneously secures the elbows and the chest of said patient against movement when applied.

14. The immobilizer of claim 11 including:

first strap means extending laterally across a portion of said restraining means;

second strap means axially fixed to said flexible member and extending beneath said first strap means, whereby the longitudinal position of said restraining means is adjusted by sliding said restraining means along said second strap means.

15. The immobilizer of claim 1 wherein:

said restraining means extends from said flexible member and includes a first flexible strap positioned to secure the arms and chest of the patient against relative movement, and a second flexible strap positioned to secure the legs of the patient against relative movement, whereby the patient may bend at the thighs and/or knees while restrained in said immobilizer and said rigid radiotransparent backing member is removed from said flexible member.

16. The immobilizer of claim 15 including:

third restraining means for securing the head of said patient against movement relative to said flexible member.

17. The immobilizer of claim 15 including:

third restraining means adapted to secure the thighs of said patient against movement relative to said flexible member.

18. The immobilizer of claim 15 including third restraining means adapted to secure the torso of said patient against movement relative to said flexible member.

19. The immobilizer of claim 1 wherein said flexible radiotransparent member including said restraining means is composed of a disposable material.

20. The immobilizer of claim 1 wherein:

said flexible member includes a pair of slots adjacent the upper portion thereof;

head restraining means mounted upon a longitudinal strap;

said longitudinal strap extending through said slots whereby one end of said strap loops back into contact with a central portion of said longitudinal strap;

self attachment means on said one end of said longitudinal strap to removably adhere said end of said strap to said central portion of said strap;

said head restraining means including laterally extending strap means for engaging the forehead of said patient; and longitudinally extending strap means extending around the head of said patient.

21. An immobilizer for use in X-ray or surgical procedures on a patient comprising:
a flexible radiotransparent member having front and posterior surfaces;
a rigid radiotransparent backing member removably attached to one of said surfaces of said flexible member to provide a rigid support therefore;
said flexible member including at least one pair of strap means extending therefrom, said strap means having self attachment means at the ends thereof;
said strap means also including slots which receive an end of one of said straps after said strap has passed around a limb of said patient, whereby said strap is capable of being positioned in said slot to secure any size limb against movement relative to said backing member.

22. The immobilizer of claim 21 including an additional pair of strap means extending from said flexible member and adapted to extend around and be secured adjacent an additional portion of said patient, whereby said limb and said additional portion of said patient are secured against relative movement.

* * * * *